United States Patent [19]

Itagaki et al.

[11] Patent Number: 4,976,921

[45] Date of Patent: * Dec. 11, 1990

[54] KIT FOR CONTACT LENS STERILIZATION AND METHOD FOR CONTACT LENS STERILIZATION

[75] Inventors: Yoko Itagaki, Kodama; Masahiro Hiranuma, Honjo, both of Japan

[73] Assignee: Hoya Corporation, Tokyo, Japan

[ * ] Notice: The portion of the term of this patent subsequent to Oct. 25, 2005 has been disclaimed.

[21] Appl. No.: 283,861

[22] Filed: Dec. 13, 1988

[30] Foreign Application Priority Data

Dec. 18, 1987 [JP] Japan ................................ 62-320460

[51] Int. Cl.$^5$ ............................................... A61L 2/16
[52] U.S. Cl. ......................................... 422/28; 422/30; 422/37; 422/40; 422/61; 436/1; 436/79; 436/125; 436/177; 436/826; 134/26; 134/42; 252/95; 252/90; 252/105; 252/106; 252/174.13
[58] Field of Search ................. 422/28, 30, 37, 40, 422/61; 436/1, 79, 124–125, 177, 826; 134/42, 26; 252/95, 90, 105, 106, 174.13

[56] References Cited

U.S. PATENT DOCUMENTS

| | | | |
|---|---|---|---|
| 4,312,833 | 1/1982 | Clough et al. | 422/30 |
| 4,490,389 | 12/1984 | Nelson et al. | 422/28 X |
| 4,568,517 | 2/1986 | Kaspar et al. | 422/301 X |
| 4,614,549 | 9/1986 | Ogunbiyi et al. | 422/28 X |
| 4,780,152 | 10/1988 | Itagaki et al. | 422/37 X |
| 4,863,627 | 9/1989 | Davies et al. | 422/28 X |

*Primary Examiner*—Robert J. Warden
*Assistant Examiner*—Lynn M. Kummert
*Attorney, Agent, or Firm*—Nixon & Vanderhye

[57] ABSTRACT

Contact lenses can be sterilized effectively in a short time, by using a kit for contact lens sterilization which comprises an oxidizing agent for sterilizing contact lenses and a reducing agent for making nontoxic the oxidizing agent still remaining after sterilization and wherein the oxidizing agent and the reducing agent each have such a property and form that they do not substantially react with each other in the kit and that when they are placed in water substantially simultaneously, the major portion of the oxidizing agent dissolves in water more rapidly than the major portion of the reducing agent. Further, with this kit, the sterilized contact lenses can be made nontoxic without fail.

16 Claims, No Drawings

KIT FOR CONTACT LENS STERILIZATION AND METHOD FOR CONTACT LENS STERILIZATION

BACKGROUND OF THE INVENTION

1. Field of the Invention

The present invention relates to a kit for contact lens sterilization, as well as to a method for contact lens sterilization. The present invention is applied to sterilization of known contact lenses composed mainly of, for example, methyl methacrylate, silicone-containing methacrylate, hydroxyethyl methacrylate, butyl acrylate or the like.

2. Description of the Related Art

Methods for sterilizing contact lenses to kill bacteria and Eumycetes adhering thereto are already known and various compositions have been proposed for this purpose.

For example, Japanese Patent Application Kokai (Laid-Open) No. 132115/1982 discloses a method for contact lens sterilization by the use of a chlorhexidine salt as a disinfectant. However, when this method is applied to the repeated treatment of a soft contact lens, even if the chlorhexidine salt is used in a low concentration, there occurs adsorption and accumulation of the salt by and on the lens because of the properties of the soft contact lens; hence, it is feared that the disinfectant accumulated and concentrated on the lens during the use of the lens is released from the lens and causes damage to the cornea. Japanese Patent Application Kokai (Laid-Open) No. 105457/1984 discloses a method for contact lens sterilization wherein a contact lens is sterilized with hydrogen peroxide and, after the completion of the sterilization, the lens is immersed in a sodium pyruvate solution to neutralize the remaining hydrogen peroxide. These methods, however, are defective in that the treatment for making nontoxic the disinfectant remaining on the contact lens may be forgotten and the visual check of the completion timing of such a treatment is difficult.

Thus, the conventional methods for contact lens sterilization have a sufficient sterilization effect but have drawbacks, for example, in that the safety of sterilized lens is low, that the sterilization operation becomes lengthy because two disinfecting components are added separately, that the addition of one disinfecting component is forgotten resulting in the reduced safety of sterilized lens, and that the safety of sterilized lens cannot be ascertained.

SUMMARY OF THE INVENTION

An object of the present invention is to provide a novel kit for contact lens sterilization which can kill bacteria and Eumycetes adhering to contact lenses, effectively in a short time, which can reliably conduct, after the killing, a treatment for making the sterilized lenses nontoxic, and which can easily and visually check the completion timing of said treatment for making the sterilized lenses nontoxic, as well as a method for contact lens sterilization using said kit.

Another object of the present invention is to provide a kit for contact lens sterilization which can conduct both contact lens sterilization and a treatment for making the sterilized lens nontoxic in a single sterilization operation and makes safe the possible wearing of the resulting lens right after the operation without washing the lens with a running water (tap water, purified water), as well as to a method for contact lens sterilization using said kit.

Still another object of the present invention is to provide a kit for contact lens sterilization which gives no adverse effect on the shape, color tone, etc. of contact lens even when the lens is subjected to repeated sterilization with the kit and accordingly which can conduct the sterilization of contact lens safely and reliably, as well as a method for contact lens sterilization using said kit.

These objects of the present invention can be achieved by the following kit and method for contact lens sterilization.

According to the present invention, there are provided a kit for contact lens sterilization, comprising an oxidizing agent for sterilizing contact lenses and a reducing agent for making nontoxic the oxidizing agent still remaining after sterilization, wherein the oxidizing agent and the reducing agent each have such a property and form that they do not substantially react with each other in the kit and that when they are placed in water substantially simultaneously, the major portion of the oxidizing agent dissolves in the water more rapidly than the major portion of the reducing agent, and a method for contact lens sterilization by using an oxidizing agent for sterilizing contact lenses and a reducing agent for making nontoxic the oxidizing agent still remaining after sterilization, the oxidizing agent and the reducing agent each having such a property and form that they do not substantially react with each other in the kit and that when they are placed in water substantially simultaneously, the major portion of the oxidizing agent dissolves in the water more rapidly than the major portion of the reducing agent, the method comprising placing the oxidizing agent and the reducing agent in water substantially simultaneously to dissolve the major portion of the oxidizing agent more rapidly than the major portion of the reducing agent and immediately conducting a sterilization treatment of contact lens by the oxidizing agent and a treatment of the residual oxidizing agent by the reducing agent for making the residual oxidizing agent nontoxic, macroscopically in this order.

DESCRIPTION OF THE PREFERRED EMBODIMENT

The present invention will be explained specifically.

The oxidizing agent which is a first essential component in the kit for contact lens sterilization according to the present invention is to kill bacteria and Eumycetes adhering to contact lenses. It is preferably compounds capable of releasing available chlorine, such as bleaching powder (chlorinated lime), chloramine, chloramine T, chloramine B, halazone, calcium hypochlorite, chlorinated isocyanuric acid and the like. Of these, the bleaching powder, chloramine T and chlorinated isocyanuric acid are especially preferable.

The reducing agent which is a second essential component in the kit for contact lens sterilization according to the present invention is to make nontoxic the oxidizing agent still remaining after sterilization. It is preferably sodium thiosulfate, or hydroxycarboxylic acids and salts thereof, such as citric acid, malic acid, tartaric acid, ascorbic acid, and their sodium, potassium, calcium and other salts. Of these, sodium thiosulfate, citric acid, sodium citrate and ascorbic acid are especially preferable.

As the kit containing the oxidizing agent and the reducing agent, there can be mentioned a package. The package has no particular restriction as long as it is made of a material giving substantially no adverse effect on the oxidizing agent and the reducing agent. Typical examples of the package include a three sides-sealed aluminum package, a stick-shaped aluminum package and a moistureproof plastic container. As the kit, there can also be mentioned a capsule containing the oxidizing agent and the reducing agent. Such a capsule has no restriction as long as it is water-soluble.

Each of the oxidizing agent and the reducing agent constituting the kit of the present invention must take a form satisfying both of the following requirements (I) and (II).

(I) The oxidizing agent and the reducing agent do not substantially react with each other in the kit, for example, a package.

(II) When the kit, for example, a package is opened and each component is placed in water, the major portion of the oxidizing agent dissolves in the water more rapidly than the major portion of the reducing agent.

In the requirement (I), "do not substantially react with each other" implies that the oxidizing agent and the reducing agent do not at all or do not substantially react with each other while they are contained in the kit, for example, a package, so that they can achieve respective intended purposes (a sterilization treatment of lens in the case of the oxidizing agent and a treatment of the residual oxidizing agent for making it nontoxic in the case of the reducing agent) when the kit, for exmaple, a package is opened and each component is placed in water. Accordingly, even if a very small portion of the oxidizing agent and a very small portion of the reducing agent make mutual contact in the kit, for exmaple, a package to cause an extremely low level of reaction, it is no problem as long as the residual unreacted oxidizing agent and the residual unreacted reducing agent can achieve respective intended purposes when they are placed in water.

In the requirement (II), "the major portion of the oxidizing agent dissolves in water more rapidly than the major portion of the reducing agent" implies that when they are placed in water substantially simultaneously, the dissolution peak of the oxidizing agent appears earlier than the dissolution peak of the reducing agent. Accordingly, even if both the dissolution of the oxidizing agent and the dissolution of the reducing agent start simultaneously at a certain timing after they have been placed in water, it is no problem as long as macroscopically the sterilization treatment of contact lens by the oxidizing agent takes place first and the treatment of the residual oxidizing agent by the reducing agent for making the residual oxidizing agent nontoxic takes place next.

In order for the oxidizing agent and the reducing agent to satisfy the requirements (I) and (II), it is preferred that the oxidizing agent be in a form of powders or granules and the reducing agent be in a form of tablets. The reason is that the oxidizing agent and the reducing agent, when each is in said form as compared with when both of them are in a form of powders or granules, have a low degree of mutual contact and do not substantially react with each other in the kit and, when they are placed in water, the oxidizing agent in powder or granule form dissolves in the water more rapidly than the reducing agent in tablet form.

When the oxidizing agent is used in a form of powders or granules, it is possible to add an excipient such as NaCl, KCl, lactose and/or dextrose or the like in order to make measuring easier.

When the reducing agent is used in a form of tablets, coating of the tablets with a coating agent is particularly preferable because it can completely prevent the direct reaction between the oxidizing agent and the reducing agent in the kit, for example, a package and moreover, when they are placed in water, the reducing agent can start dissolution, after the oxidizing agent has sufficiently achieved its purpose, to conduct a treatment of the residual oxidizing agent for making it nontoxic (whereby the simultaneous occurrence of (a) lens sterilization by the oxidizing agent and (b) a treatment of the residual oxidizing agent by the reducing agent can be minimized and the two components can be utilized efficiently).

As the coating agent, there are preferred, for example, carboxymethylethylcellulose, cellulose acetate phthalate, hydroxypropylmethylcellulose phthalate, a methacrylic acid-ethyl acrylate copolymer and a methacrylic acid-methyl acrylate copolymer. Any coating agent can be used as long as it is soluble in aqueous solutions having a pH of 5.5 or above.

Tablets containing the reducing agent are preferably effervescent tablets in order to reliably conduct a treatment of the residual oxidizing agent for making it nontoxic. The component added to make tablets effervescent include sodium bicarbonate, potassium bicarbonate, etc. Any of these components can achieve a purpose of foaming. The talbets may further contain a lubricant, a disintegrating agent, etc., ordinarily used in tablet preparation.

In order to satisfy the requirements (I) and (II), the oxidizing agent and the reducing agent can also be in such a form that both of them are in a form of powders or granules and, in order to avoid their mutual contact, the reducing agent is contained in a bag or coated with a coating agent. In this case as well, when the kit (e.g. a package) containing the oxidizing agent and the reducing agent is placed in water, the oxidizing agent dissolves in the water more rapidly than the reducing agent contained in a bag or coated with a coating agent, whereby the object of the present invention can be achieved.

The bag has no particular restriction as long as it is soluble in aqueous solutions having a pH of 5.5 or above. The coating agent used for coating the reducing agent of powder or granule form can be same as that used for coating the tablets.

Even if the oxidizing agent and the reducing agent take the same form, if the former can dissolve in water more rapidly than the latter, they can be used as they are, in the kit.

The method for contact lens sterilization using the kit of the present invention will be described. The concentration of the oxidizing agent after dissolution in water is preferably 0.0005–5.0% by w/v ordinarily. When the oxidizing agent is, for example, bleaching powder (chlorinated lime) which is a compound capable of releasing available chlorine, the concentration of the bleaching powder during the sterilization treatment is suitably 1.0–0.001% by w/v after dissolution in water. When the concentration is lower than 0.001% by w/v, the effect of the bleaching powder is small and a treatment of long time is required. When the concentration is higher than 1.0% by w/v, no corresponding increase in effect is obtained. A more preferable concentration of the bleaching powder is 0.5-0.1% by w/v after dissolution in water.

The concentration of the reducing agent during use must be such that it provides an amount sufficient for the reduction of the residual oxidizing agent (compound capable of releasing available chlorine) and yet gives no effect on the pH and osmotic pressure of the solution after treatment. The concentration of the reducing agent after dissolution in water is preferably 0.005-10.0% by w/v ordinarily. When the reducing agent is, for example, sodium thiosulfate, citric acid or sodium citrate, their concentrations after dissolution in water are preferably 2.0-0.01% by w/v (sodium thiosulfate), 2.0-0.01% by w/v (citric acid) and 5.0-0.05% by w/v (sodium citrate), more preferably 1.0-0.2% by w/v (sodium thiosulfate), 1.0-0.2% by w/v (citric acid) and 3.0-1.0% by w/v (sodium citrate).

Based on these concentrations after dissolution in water, the amounts of the oxidizing agent and the reducing agent in a kit are determined.

According to the method for contact lens sterilization using the kit of the present invention, when the oxidizing agent and the reducing agent are placed in water substantially simultaneously, the major portion of the oxidizing agent dissolves in water more rapidly than the major portion of the reducing agent because the oxidizing agent and the reducing agent have the above mentioned properties or forms. As a result, the oxidizing agent starts sterilization of contact lens; simultaneously, the reducing agent begins to dissolve in water slowly; and after the oxidizing agent has achieved its purpose of killing bacteria and Eumycetes adhering to a contact lens, the reducing agent treats the residual oxidizing agent to make it nontoxic. The treatment of the residual oxidizing agent by the reducing agent to make the former nontoxic is complete when the reducing agent has dissolved completely. When the reducing agent is tablets, the timing of complete dissolution of the reducing agent can be confirmed definitely by visually checking the complete disappearance of the tablets. Therefore, a reducing agent in tablet form is preferred particularly.

In a preferred embodiment of the present invention wherein the reducing agent is coated tablets, firstly the oxidizing agent dissolves and starts sterilization of contact lens; simultaneously, the coating agent on tablets begins to dissolve slowly; in a few minutes to half an hour, the reducing agent present in tablets begins to dissolve slowly while foaming in the case of, for example, effervescent tablets and starts a reaction with the residual oxidizing agent to make it nontoxic. Thus, the sterilization treatment of contact lens by the oxidizing agent and the treatment of the residual oxidizing agent by the reducing agent for making the residual oxidizing agent nontoxic are conducted in different time spans and this is preferable particularly.

The sterilization method of the present invention can be applied to sterilization of all known contact lenses. It is desired, however, that the solution after treatment be isotonic with and has the same pH as the human lacrima in view of (a) the fact that in particular, hydrogel contact lenses composed mainly of hydroxyethyl methacrylate or the like may undergo shape change by the osmotic pressure, pH, etc. of treating solution used and (b) the compatibility of sterilized contact lens with eyes. For this purpose, it is possible to add to the oxidizing agent and the reducing agent, tonicity agents such as NaCl, KCl, glucose and the like and buffer agents such as boric acid, sodium borate, sodium hydrogenphosphate, sodium acetate, sodium carbonate and the like, all employed ordinarily.

The kit of the present invention is used in the following manner periodically, for examle, daily, weekly, biweekly or monthly. That is, a contact lens is removed from eyes, washed with water gently, and then immersed for 15 to 60 minutes in a container containing a required volume of water (tap water or purified water) to which one pack of the kit of the present invention has been added. In the early period of the immersion, the bacteria and Eumycetes adhering to the contact lens are killed by the oxidizing agent; then, the reducing agent dissolves slowly and completes a treatment for making the residual oxidizing agent nontoxic. When the reducing agent takes a form of tablets, the completion timing of the treatment of the residual oxidizing agent by the reducing agent for making the residual oxidizng agent nontoxic can be clearly confirmed visually by the disappearance of tablets in treating solution. When the treatment is over, the lens is worn or stored in a special preservative solution. If the lens is worn directly after the treatment with the kit of the present invention, it is safe because there is no damage to eyes.

Repeated sterilization of a contact lens with the kit of the present invention has no effect on the shape, color tone, etc. of the lens. Accordingly, the lens sterilization by the kit of the present invention is very safe from this aspect.

The present invention will be explained in further detail by way of Examples.

EXAMPLE 1

| Powder composition | |
|---|---|
| Chlorinated lime as a compound capable of releasing available chlorine | 0.035 g |
| Lactose (excipient) | 0.30 g |
| Tablet composition | |
| Citric acid (reducing agent) | 0.06 g |
| Sodium citrate (pH-adjusting agent and reducing agent) | 0.12 g |
| Sodium bicarbonate (foaming agent and pH-adjusting agent) | 0.10 g |
| Magnesium stearate (lubricant) | 0.0014 g |
| Carboxymethylethylcellulose (coating agent for tablets) | 0.02 g |

Powders and coated tablets each having the above composition were prepared according to ordinary methods. They were packed in a three sides-sealed aluminum package to obtain a kit of the present invention.

EXAMPLE 2

| Powder composition | |
|---|---|
| Chlorinated lime as a compound capable of releasing available chlorine | 0.0045 g |
| Lactose (excipient) | 0.20 g |
| Tablet composition | |
| Sodium thiosulfate (reducing agent) | 0.005 g |
| sodium citrate (reducing agent and pH-adjusting agent) | 0.15 g |
| Sodium bicarbonate (foaming agent and pH-adjusting agent) | 0.10 g |
| Magnesium stearate (lubricant) | 0.0007 g |
| Polyethylene glycol 6000 (lubricant) | 0.01 g |
| Carboxymethylethylcellulose (coating agent for tablets) | 0.015 g |

Powders and coated tablets each having the above composition were prepared according to ordinary methods. They were packed in a stick-shaped aluminum package to obtain a kit of the present invention.

EXAMPLE 3

| Powder composition | |
|---|---|
| Chlorinated lime as a compound capable of releasing available chlorine | 0.045 g |
| Dextrose (excipient) | 0.20 g |
| Tablet composition | |
| Citric acid (reducing agent) | 0.08 g |
| Sodium citrate (reducing agent and pH-adjusting agent) | 0.15 g |
| Potassium bicarbonate (foaming agent and pH-adjusting agent) | 0.10 g |
| Magnesium stearate (lubricant) | 0.0007 g |
| Polyethylene glycol 6000 (lubricant) | 0.01 g |
| Carboxymethylethylcellulose (coating agent for tablets) | 0.015 g |

Powders and coated tablets each having the above composition were prepared according to ordinary methods. They were packed in a stick-shaped aluminum package to obtain a kit of the present invention.

EXAMPLE 4

| Powder composition | |
|---|---|
| Chloramine T as a compound capable of releasing available chlorine | 0.10 g |
| Lactose (excipient) | 0.10 g |
| Tablet composition | |
| Ascorbic acid (reducing agent) | 0.01 g |
| Sodium citrate (reducing agent and pH-adjusting agent) | 0.10 g |
| Sodium bicarbonate (foaming agent and pH-adjusting agent) | 0.12 g |
| Talc (lubricant) | 0.003 g |
| Methacrylic acid-ethyl acrylate copolymer (coating agent for tablets) | 0.03 g |

Powders and coated tablets each having the above composition were prepared according to ordinary methods. They were packed in a moistureproof plastic container to obtain a kit of the present invention.

EXAMPLE 5

The kits obtained in Examples 1–4 were examined for sterilizing power. That is, a suspension of a microbial count of $10^6$/ml was prepared; each of the kits obtained in Examples 1–4 was dissolved in 10 ml of the suspension; after the complete dissolution of the kit, 1.0 ml of the resulting liquid was taken and tested for survival of microbe according to the test method specified by the Pharmacopoeia of Japan.

The results are shown in Table 1.

TABLE 1

| Microbe used | Example 1 kit | Example 2 kit | Example 3 kit | Example 4 kit |
|---|---|---|---|---|
| S. aureus (ATCC 6538) | Negative | Negative | Negative | Negative |
| P. aeruginosa (ATCC 9027) | Negative | Negative | Negative | Negative |
| E. coli (ATCC 8739) | Negative | Negative | Negative | Negative |
| C. albicans (ATCC 10231) | Negative | Negative | Negative | Negative |
| A. niger (ATCC 16404) | Negative | Negative | Negative | Negative |

As is clear from Table 1, the sterilizing powers of the kits of Examples 1–4 were confirmed.

EXAMPLE 6

A suspension of a microbial count of $10^6$/ml was prepared. A contact lens was immersed in 10 ml of the suspension and was allowed to stand overnight. The lens was taken out from the suspension and then treated with one of the kits of Examples 1–4. Thereafter, the lens was tested for survival of microbe according to the test method specified by the Pharmocopoeia of Japan.

The results are shown in Table 2.

TABLE 2

| Lens used | Example 1 kit | | Example 2 kit | | Example 3 kit | | Example 4 kit | |
|---|---|---|---|---|---|---|---|---|
| | S. aureus | C. albicans | P. aeruginosa | A. niger | E. coli | C. albicans | E. coli | A. niger |
| HOYA Hard | Negative | Negative | Negative | Negative | Negative | Negative | Negative | Negative |
| HOYA Hard OP | Negative | Negative | Negative | Negative | Negative | Negative | Negative | Negative |
| HOYA Hard 58 | Negative | Negative | Negative | Negative | Negative | Negative | Negative | Negative |
| HOYA Soft | Negative | Negative | Negative | Negative | Negative | Negative | Negative | Negative |
| HOYA Soft T40 | Negative | Negative | Negative | Negative | Negative | Negative | Negative | Negative |

As is clear from Table 2, it was confirmed that the kits of Examples 1–4 had a sterilizing power for contact lenses stained with various microbes.

EXAMPLE 7

Various contact lenses were actually applied to eyes and stained. Then, only the left eye lenses (L) were treated with the kits obtained in Examples 1–4. (The right eye lenses (R) were not treated.) Thereafter, both the left eye lenses (L) and the right eye lenses (R) were tested for survival of microbe according to the test method specified by the Pharmocopoeia of Japan.

The results are shown in Table 3.

TABLE 3

| Lens used | | Example 1 kit | Example 2 kit | Example 3 kit | Example 4 kit |
|---|---|---|---|---|---|
| HOYA Hard | R | Positive | Positive | Positive | Positive |
| | L | Negative | Negative | Negative | Negative |
| HOYA Hard OP | R | Positive | Positive | Positive | Positive |
| | L | Negative | Negative | Negative | Negative |
| HOYA Hard 58 | R | Positive | Positive | Positive | Positive |
| | L | Negative | Negative | Negative | Negative |
| HOYA Soft | R | Positive | Positive | Positive | Positive |
| | L | Negative | Negative | Negative | Negative |
| HOYA Soft T40 | R | Positive | Positive | Positive | Positive |
| | L | Negative | Negative | Negative | Negative |

As is clear from Table 3, it was confirmed that the kits of Examples 1-4 had a sterilizing power also for contact lenses stained by actual application to eyes.

EXAMPLE 8

Contact lenses (HOYA Soft, HOYA Soft T40, HOYA Hard, HOYA Hard OP and HOYA Hard 58) were subjected to a repeated treatment with each of the kits of Examples 1-4, and its effect on lens shape was examined. The results are shown in Table 4.

A hard contact lens (HOYA Hard), an oxygen-permeable hard contact lens (a product of A Company) and two oxygen-highly-permeable hard contact lenses (HOYA Hard 58 and a product of A Company) were subjected to a repeated treatment with each of the kits of Examples 1-4, and its effect on discoloration of lens was examined. The results are shown in Table 5.

color reaction by o-toluidine hydrochloride. In all the cases of Examples 1-4, the solutions after treatment gave no color development indicating presence of residual available chlorine. In contrast, all of the treating solutions containing only powders and containing no tablets gave distinct color development. The solution after treatment when the kits of the present invention were used, were dropped in eyes, but there was neither stimulus nor damage to the cornea.

Thus, it was confirmed that the treating solution using the kit of the present invention gives no damage to eyes and is safe.

What we claim is:

1. A kit for contact lens cleaning, comprising a compound capable of releasing available chlorine as an oxidizing agent for removing stains adhering to contact lenses and a reducing agent for making nontoxic the

TABLE 4

| | | Soft contact lens | | | | Hard contact lens | | Oxygen-permeable hard contact lens | | Oxygen-highly-permeable hard contact lens | |
|---|---|---|---|---|---|---|---|---|---|---|---|
| | | HOYA Soft | | HOYA Soft T40 | | HOYA Hard | | HOYA Hard OP | | HOYA Hard 58 | |
| | | Before treatment | After 100 times treatment | Before treatment | After 100 times treatment | Before treatment | After 100 times treatment | Before treatment | After 100 times treatment | Before treatment | After 100 times treatment |
| Example 1 kit | BC*[1] | 8.4 | 8.4 | 8.1 | 8.1 | 7.60 | 7.60 | 7.40 | 7.40 | 7.85 | 7.85 |
| | Power*[2] | −2.50 | −2.25 | −3.00 | −2.75 | −8.00 | −8.00 | +8.00 | +8.00 | −3.25 | −3.25 |
| | Size*[3] | 13.3 | 13.2 | 13.3 | 13.1 | 8.8 | 8.8 | 8.5 | 8.5 | 8.8 | 8.8 |
| | Thickness*[4] | 0.20 | 0.19 | 0.06 | 0.05 | 0.08 | 0.08 | 0.42 | 0.42 | 0.13 | 0.13 |
| Example 2 kit | BC | 8.1 | 8.1 | 8.7 | 8.7 | 8.00 | 8.00 | 7.20 | 7.20 | 7.50 | 7.50 |
| | Power | −3.00 | −3.00 | −8.00 | −8.00 | −3.00 | −3.00 | −15.00 | −15.00 | −6.00 | −6.00 |
| | Size | 13.3 | 13.3 | 13.3 | 13.3 | 8.8 | 8.8 | 8.5 | 8.5 | 8.8 | 8.8 |
| | Thickness | 0.16 | 0.16 | 0.06 | 0.06 | 0.08 | 0.08 | 0.08 | 0.08 | 0.08 | 0.08 |
| Example 3 kit | BC | 8.1 | 8.1 | 8.7 | 8.7 | 8.00 | 8.00 | 7.20 | 7.20 | 7.85 | 7.85 |
| | Power | −3.00 | −3.00 | −8.00 | −8.00 | −3.00 | −3.00 | −15.00 | −15.00 | −3.00 | −3.00 |
| | Size | 13.3 | 13.3 | 13.3 | 13.3 | 8.8 | 8.8 | 8.5 | 8.5 | 8.8 | 8.8 |
| | Thickness | 0.16 | 0.16 | 0.06 | 0.06 | 0.08 | 0.08 | 0.08 | 0.08 | 0.13 | 0.13 |
| Example 4 kit | BC | 8.7 | 8.7 | 8.4 | 8.4 | 7.20 | 7.20 | 8.00 | 8.00 | 8.15 | 8.15 |
| | Power | −4.50 | −4.25 | +3.00 | +3.00 | +3.00 | +3.00 | −3.00 | −3.00 | −3.00 | −3.00 |
| | Size | 13.3 | 13.4 | 13.3 | 13.4 | 8.8 | 8.8 | 8.5 | 8.5 | 8.8 | 8.8 |
| | Thickness | 0.16 | 0.17 | 0.19 | 0.20 | 0.29 | 0.29 | 0.13 | 0.13 | 0.13 | 0.13 |

*[1]BC ... Base curve of lens (curvature at the back side)
*[2]Power ... Refraction power of lens at the apex
*[3]Size ... Diameter of lens
*[4]Thickness ... Thickness of lens

TABLE 5

| | Color tone after 100 times treatment with: | | | |
|---|---|---|---|---|
| | Example 1 kit | Example 2 kit | Example 3 kit | Example 4 kit |
| HOYA Hard (light green) | No change of color tone (light green) | Same as left | Same as left | Same as left |
| Oxygen-permeable hard contact lens (product of A Company) (light gray) | No change of color tone (light gray) | Same as left | Same as left | Same as left |
| HOYA Hard 58 (light blue) | No change of color tone (light blue) | Same as left | Same as left | Same as left |
| Oxygen-highly-permeable hard contact lens (product of A Company) (light blue) | No change of color tone (light blue) | Same as left | Same as left | Same as left |

As is clear from Tables 4 and 5, in repeated sterilization of contact lenses using the kits of Examples 1-4, neither parameter changes nor discoloration occurred in any lenses. Thus, it was confirmed that the kit of the present invention has no effect on the shape, etc. of contact lens.

Next, when the kits of Examples 1-4 were used, the amount of available chlorine remaining in the solution after treatment was measured in accordance with the oxidizing agent still remaining after stain removal, wherein the oxidizing agent and the reducing agent are each in such a form that the oxidizing agent and the reducing agent do not substantially react with each other in the kit and that when they are placed in water substantially simultaneously, the major portion of the oxidizing agent dissolves int he water more rapidly than the major portion of the reducing agent.

2. A kit according to claim 1, wherein the oxidizing agent is in a form of powders or granules and the reducing agent is in a form of tablets.

3. A kit according to claim 2, wherein the tablets are coated with a coating agent.

4. A kit according to claim 2, wherein the tablets are effervescent tablets.

5. A kit according to claim 1, wherein the oxidizing agent and the reducing agent are each in a form of powders or granules and further the reducing agent is contained in a bag or coated with a coating agent.

6. A kit according to claim 1, wherein the oxidizing agent and the reducing agent are contained in a single package.

7. A kit according to claim 6, wherein the package is selected from the group consisting of a three sides-sealed aluminum package, a stick-shaped aluminum package and a moistureproof plastic container.

8. A kit according to claim 1, wherein the reducing agent is a hydroxycarboxylic acid or a salt thereof, or sodium thiosulfate.

9. A method for contact lens cleaning using a compound capable of releasing available chlorine as an oxidizing agent for removing stains adhering to contact lenses and a reducing agent for making nontoxic the oxidizing agent still remaining after stain removal, the oxidizing agent and the reducing agent being each in such a form that when they are placed in water substantially simultaneously, the major portion of the oxidizing agent dissolves in the water more rapidly than the major portion of the reducing a gent, the method comprising:

(1) placing the oxidizing agent and the reducing agent in water substantially simultaneously to dissolve the major portion of the oxidizing agent;

(2) immediately conducting a cleaning treatment of the lens by oxidizing the agent and a treatment of the residual oxidizing agent by the reducing agent for making the residual oxidizing agent nontoxic, macroscopically in this order.

10. A method according to claim 9, wherein the oxidizing agent is in a form of powders or granules and the reducing agent is in a form of tablets.

11. A method according to claim 10, wherein the tablets are coated with a coating agent.

12. A method according to claim 10, wherein the tablets are effervescent tablets.

13. A method according to claim 9, wherein the oxidizing agent and the reducing agent are each in a form of powders or granules and further the reducing agent is contained in a bag or coated with a coating agent.

14. A method according to claim 9, wherein the treating solution after the completion of sterilization is isotonic with and has the same pH as the human lacrima.

15. A method according to claim 9, wherein the concentration of the oxidizing agent after dissolution in water is 0.0005–5.0% by w/v.

16. A method according to claim 9, wherein the concentration of the reducing agent after dissolution in water is 0.005–10.0% by w/v.

* * * * *